United States Patent
Pangrazi et al.

(10) Patent No.: US 6,918,305 B2
(45) Date of Patent: Jul. 19, 2005

(54) TEST FOR MEASURING ADHESION OF POLYMER BINDERS TO A HEATED METAL SURFACE

(75) Inventors: Ronald Joseph Pangrazi, Fleetwood, PA (US); Beth Rene' Spivak, Souderton, PA (US); John Joseph Halat, Breinigsville, PA (US); Joel Erwin Goldstein, Allentown, PA (US)

(73) Assignee: Air Products Polymers, L.P., Allentown, PA (US)

( * ) Notice: Subject to any disclaimer, the term of this patent is extended or adjusted under 35 U.S.C. 154(b) by 135 days.

(21) Appl. No.: 10/024,967

(22) Filed: Dec. 19, 2001

(65) Prior Publication Data

US 2003/0110866 A1 Jun. 19, 2003

(51) Int. Cl.$^7$ .................................................. G01N 3/08
(52) U.S. Cl. ........................................................ 73/827
(58) Field of Search .......................... 73/827, 834, 835, 73/826, 830, 838, 841

(56) References Cited

U.S. PATENT DOCUMENTS

| 3,580,065 A | * | 5/1971 | Strittmater et al. ....... 73/150 R |
| 4,893,513 A | | 1/1990 | Schroeder et al. |
| 4,899,581 A | | 2/1990 | Allen et al. |
| 5,280,717 A | | 1/1994 | Hoseney et al. |
| 5,744,703 A | | 4/1998 | Krenceski et al. .......... 73/54.01 |
| 6,107,222 A | | 8/2000 | Joseph et al. ................ 442/412 |
| 6,313,448 B1 | * | 11/2001 | Johnson ....................... 219/633 |
| 6,451,155 B1 | * | 9/2002 | Toy et al. .................... 156/325 |
| 6,455,152 B1 | * | 9/2002 | DiZio et al. ................. 428/345 |

FOREIGN PATENT DOCUMENTS

EP          1 158 290 A       11/2001

* cited by examiner

*Primary Examiner*—Max Noori
(74) *Attorney, Agent, or Firm*—Mary E. Bongiorno

(57) ABSTRACT

The following method is used to measure the adhesion of a polymer binder to a heated metal surface:

A metal plate is attached to a heated (350° F.; 177° C.) platform and allowed to equilibrate to the temperature of the platform. A polymer emulsion binder is applied to a substrate, such as cotton fabric, and an end of the coated substrate is attached to a tensile measuring apparatus. The coated side of the coated substrate is pressed onto the heated metal plate; e.g., using a 3-lb lab roller. After a length of time to cause drying and/or partial cure of the binder (approximately 30 seconds), the metal plate and the tensile measuring device are separated at a given uniform speed. The amount of force needed to remove the substrate from the metal plate is recorded.

9 Claims, No Drawings

TEST FOR MEASURING ADHESION OF POLYMER BINDERS TO A HEATED METAL SURFACE

BACKGROUND OF THE INVENTION

One method of screening polymer binders for adhesion to metal surfaces, has been to place drops of the binder onto a metal panel and allowed them to dry overnight. The dried binder drops were then 'picked' off of the metal plate and rated, compared to the value assigned a control material. If the drops were as difficult or more difficult to remove from the plate than the control, the adhesion was deemed adequate. However, heat was not taken into account using this technique and actual tensile/adhesion values could not be measured. The only other way of evaluating nonwoven binders for use in a creping process has been to conduct testing at a customer site where a large amount of emulsion is needed to obtain meaningful data.

There is no known industry test for accurately testing polymer emulsion binders for adhesion to heated metal surfaces, such as surfaces used in creping processes for nonwoven webs, especially double recrepe (DRC) processes.

The release and adhesion tester, developed by the Tag and Label Manufacturer Institute (TLMI), has been used to evaluate various types of adhesion, where adhesive properties are required, such as pressure sensitive labels, diaper tabs, and the like.

Examples are Described Below:

U.S. Pat. No. 5,744,703 (1998) discloses use of a modified release and adhesion tester to measure the stringiness of room temperature vulcanizable silicone sealant compositions.

U.S. Pat. No. 6,107,222 (2000) discloses use of a release and adhesion tester to measure adhesive transfer to an applied paper when the coated sample is removed from the paper.

The use of the release and adhesion tester for evaluating adhesiveness of binders to a heated metal surface has not been reported.

BRIEF SUMMARY OF THE INVENTION

This invention is directed to a test method for measuring adhesion or peel strength of polymer binders on heated metal surfaces. The method evaluates the ability of a polymer binder, after it is applied to a substrate, to quickly adhere the substrate to a heated metal creping drum. As the substrate is brought into contact with a creping blade the adhesion between the heated drum and the substrate (resulting from the quickly drying binder) determines acceptable crepe.

In the test method of this invention, a metal plate is attached to a heated (350° F.; 177° C.) platform and allowed to equilibrate to the temperature of the platform (approximately 2 minutes). A polymer emulsion binder is applied to a substrate, such as cotton fabric, and an end of the coated substrate is attached to a tensile measuring apparatus. The coated side of the coated substrate is pressed onto the heated metal plate; e.g., using a 3-lb lab roller. After a length of time to cause drying and/or partial cure of the binder (approximately 30 seconds), the metal plate and the tensile measuring device are separated at a given uniform speed. The amount of force needed to remove the substrate from the metal plate is recorded.

This method of measuring adhesion of polymer binders on a heated surface has the following advantages over known methods:

it requires only a small amount of binder;
it is very accurate in predicting effectiveness of a binder in a creping process; and
it is quick and simple and can be done using readily available equipment

DETAILED DESCRIPTION OF THE INVENTION

The test method of this invention for measuring peel strength of polymer binders on heated metal surfaces involves the following steps:

A metal plate, such as a stainless steel plate, is attached to a heated platform and allowed to equilibrate to the temperature of the platform. The temperature of the heated platform is at least 350° F. (177° C.).

A polymer emulsion binder is applied to a substrate. The substrate can be any known substrate that is used in creping processes. Examples of appropriate substrates are paper or cotton fabric, such as bleached mercerized cotton poplin. The binder can be applied by known methods, such as wire wound rod coating, mil film applicator or lab gravure printing techniques. The binder is applied in an amount that effectively coats the substrate, e.g., 0.05 g/square inch (0.05 g/6.45 square cm).

One end of the coated substrate is attached to a tensile measuring device and then pressed onto the metal plate at minimum pressure. A lab roller can be used to press the coated substrate onto the metal plate by passing the roller back and forth over the substrate for 10 seconds. A pressure exerted by the weight of a lab roller (about 3 pounds (1.4 kg)) has been found to be sufficient to adhere a coated substrate to a stainless steel plate. After a length of time to cause drying and/or partial curing of the binder, e.g., 30 seconds, the metal plate and the tensile measuring device (to which the substrate is attached) are separated at a constant speed. The speed can vary from 12 to 1200 inches (30.48 to 3048 cm) per minute. The tensile measuring apparatus can be any known apparatus for measuring tensile strength; for example a gram tensile testing gauge from Testing Machines, Inc. The amount of force needed to remove the substrate from the metal substrate is recorded and compared to a control. The control is a binder which is known to be effective in a creping process, such as AIRFLEX® 105 vinyl acetate-ethylene (VAE) polymer emulsion binder stabilized with an APE.

The apparatus used for the test described in the example was a model number 80-14-00 Release and Adhesion Tester available from Testing Machines Inc. which was modified for the test. The modification was to equip the unit with a heated bed including thermocouple ports for uniform heating of the metal platform. Other machines could be adapted for purposes of this invention.

The invention will be further clarified by a consideration of the following example, which is intended to be purely exemplary of the use of the invention.

EXAMPLE

Polymer emulsions used in the examples were as follows:

Run 1: Control—AIRFLEX 105 VAE polymer emulsion binder, stabilized with an APE, supplied by Air Products and Chemicals, Inc.

Run 2: AIRFLEX 177 VAE polymer emulsion having an APE-free surfactant system.

The remaining polymer emulsions were prepared by emulsion polymerization of vinyl acetate, ethylene, and N-methylol acrylamide in the presence of various surfactant systems in a one-gallon stirred, stainless steel reaction vessel equipped with a jacket.

Run 4: the reaction vessel was charged initially with 883.5 g of deionized water, 126.75 g of Disponil FES 32 IS (sodium laureth sulfate containing 4 moles of ethylene oxide, supplied by Cognis), 25.625 g of Tergitol 15-S-20 (a secondary alcohol ethoxylate containing 20 moles of ethylene, supplied by Dow), 0.91 g of sodium citrate, 3.5 g of 50% aqueous citric acid, 2.3 g of 5% aqueous ferric ammonium sulfate and 312.0 g of vinyl acetate. While stirring, 240.0 g of ethylene was introduced below the surface of the liquid in the reaction vessel in order that the interpolymers would have a vinyl acetate:ethylene ratio of about 80:20. The reaction vessel was heated to 50° C. Upon equilibration, the following four aqueous solutions were intermittently added to the reaction vessel over the course of the reaction (on a delay basis); 15% sodium formaldehyde sulfoxylate (SFS), 3.0% t-butylhydroperoxide (t-bhp), 1246.0 g of vinyl acetate and 324.0 g of a 30% aqueous solution of N-methylol acrylamide (NMA). After three hours, the vinyl acetate delay was terminated, after four hours the NMA delay was complete and the other two delays continued for another 30 minutes. The reaction was terminated by cooling.

Run 3: the above procedure was the same except that the surfactants used were 76.82 g of Gemtex SC-70-P dioctyl sulfosuccinate (dissolved in propylene glycol; supplied by Finetex, Inc.) and 66.25 g of Tergitol 15-S-20, instead of 126.75 g of Disponil FES 32 IS and 25.625 g of Tergitol 15-S-20.

Run 5: the above procedure was the same, except the Disponil FES 32 IS was replaced with Rhodapex EST30 (sodium trideceth sulfate (3 moles); supplied by Rhodia).

Run 6: a commercial crosslinkable vinyl acetate-ethylene polymer emulsion binder was used.

The procedure for testing release and adhesion of each of the binders was as follows:

A 2-inch×6-inch×1/32-inch stainless steel plate was attached to a movable heated (350° F.; 177° C.) inclined (45°) metal platform and allowed to equilibrate to the temperature of the platform (2 minutes.)

Each of the polymer emulsions (approximately 0.42 g) was applied to a 1½-inch×6-inch piece of bleached, mercerized cotton poplin. The jaws of a Testing Machine, Inc. gram tensile measuring apparatus were attached to a long end of the cotton poplin. The coated side of the coated cotton poplin was then pressed onto the heated stainless steel plate with a 3-pound lab roller by rolling the lab roller back and forth over the substrate for 10 seconds. After 30 seconds, the stainless steel plate was moved away from the tensile measuring device (to which the substrate was attached) at a rate of 12 inches/minute (30.48 cm/minute). The amount of force needed to remove the cotton from the stainless steel plate was recorded and compared to Airflex 105 VAE emulsion control. The results are reported as peel (% of control) in the table below:

TABLE

| Run | Polymer Emulsion | Peel (% of control) |
| --- | --- | --- |
| 1 | Control-AIRFLEX 105 VAE emulsion (stabilized with an APE) | 100 |
| 2 | AIRFLEX 177 VAE emulsion (APE free) | 25 |
| 3 | APE-free VAE-DOSS | 85 |

TABLE-continued

| Run | Polymer Emulsion | Peel (% of control) |
| --- | --- | --- |
| 4 | APE-free VAE-Disponil FES 32 IS | 103 |
| 5 | APE-free VAE-Rhodapex EST30 | 98 |
| 6 | Competitive VAE | 53 |

DOSS = dioctyl sulfosuccinate

Binders exhibiting peel values of 35% to 200% of AIRFLEX 105 VAE control should provide sufficient adhesion to a heated creping drum for purposes of a crepe process.

What is claimed is:

1. A method for measuring adhesion of a polymer emulsion binder to a heated surface which comprises:

securing a metal plate to a heated platform, said heated platform being at a temperature of at least 350° F. (177° C.);

allowing the metal plate to equilibrate to the temperature of the heated platform;

applying a polymer emulsion binder to a substrate, wherein the substrate is used in a creping process, to form a coated substrate having a coated side and an uncoated side;

attaching an end of the coated substrate to a tensile measuring device;

pressing the coated side of the coated substrate onto the heated metal plate;

waiting a period of time to allow drying or partial curing of the binder;

separating the metal plate from the tensile measuring device at a uniform speed, said substrate attached to said tensile measuring device; and recording the force required to remove the substrate from the metal plate.

2. The method of claim 1 wherein the substrate is a paper or a cotton fabric.

3. The method of claim 1 wherein the force required to remove the substrate from the metal plate is compared to the force required to remove a substrate coated with a control binder, the control binder being useful in a creping process.

4. The method of claim 3 wherein the control binder is a vinyl acetate-ethylene polymer emulsion.

5. The method of claim 3 wherein the force required to remove the coated substrate is 35 to 200% of the substrate coated with the control binder.

6. In a method for predicting the effectiveness of a binder in a creping process, wherein the peel strength of the polymer emulsion binder on a heated metal surface is measured, the improvement which comprises:

securing a metal plate to a heated platform, said heated platform being at a temperature of at least 350° F. (177° C.);

allowing the metal plate to equilibrate to the temperature of the heated platform:

applying a polymer emulsion binder to a substrate, wherein the substrate is used in a creping process, to form a coated substrate having a coated side and an uncoated side;

attaching an end of the coated substrate to a tensile measuring device;

pressing the coated side of the coated substrate onto the heated metal plate;

waiting a period of time to allow drying or partial curing of the binder;

separating the metal plate from the tensile measuring device at a uniform speed, said substrate attached to said tensile measuring device;

recording the force required to remove the substrate from the metal plate; and comparing the force required to remove the substrate from the metal plate to a force required to remove a substrate coated with a control binder using said method, the control binder being useful in a creping process.

7. The method of claim 6 wherein the substrate is a paper or a cotton fabric.

8. The method of claim 7 wherein the control binder is a vinyl acetate-ethylene polymer emulsion.

9. The method of claim 7 wherein the force required to remove the coated substrate is 35 to 200% of the force required to remove the substrate coated with the control binder.

* * * * *